United States Patent [19]

Gane et al.

[11] 4,262,154

[45] Apr. 14, 1981

[54] PROCESS FOR THE PRODUCTION OF ETHANOL AND/OR ACETALDEHYDE BY REACTING METHANOL WITH SYNTHESIS GAS

[75] Inventors: Brian R. Gane, Weybridge; David G. Stewart, Epsom, both of England

[73] Assignee: The British Petroleum Company Limited, London, England

[21] Appl. No.: 80,476

[22] Filed: Oct. 1, 1979

[30] Foreign Application Priority Data

Oct. 3, 1978 [GB] United Kingdom ............... 39054/78

[51] Int. Cl.$^3$ ........................ C07C 27/00; C07C 29/32
[52] U.S. Cl. ..................................... 568/902; 568/487
[58] Field of Search ................................ 568/902, 909

[56] References Cited

U.S. PATENT DOCUMENTS

| | | | |
|---|---|---|---|
| 3,239,570 | 3/1966 | Slaugh et al. | 568/909 |
| 3,248,432 | 4/1966 | Riley et al. | 568/902 |
| 3,401,204 | 9/1968 | Mason et al. | 568/909 |
| 3,448,157 | 6/1969 | Slaugh et al. | 568/909 |
| 3,954,877 | 5/1976 | Gipson | 568/909 |
| 4,133,966 | 1/1979 | Pretzer et al. | 568/902 |

OTHER PUBLICATIONS

Wender et al., "Science", vol. 113, (1951), pp. 206–207.

*Primary Examiner*—Joseph E. Evans

*Attorney, Agent, or Firm*—Brooks, Haidt, Haffner & Delahunty

[57] ABSTRACT

Ethanol and/or acetaldehyde is (are) produced by reacting methanol and synthesis gas at elevated temperature and pressure in the presence of a catalyst consisting of (a) cobalt, (b) an iodide or a bromide and (c) a polydentate ligand wherein the donor atoms are selected from nitrogen, phosphorus, arsenic, antimony and bismuth, ethanol being the predominant product when the donor atoms are exclusively nitrogen or phosphorus, particularly phosphorus, and acetaldehyde being the major product when the donor atoms are exclusively arsenic, antimony or bismuth. A particularly effective polydentate ligand is one having the formula:

$$(R^1)(R^2)X-[C(R^5)(R^6)]_n-Y(R^3)(R^4) \quad \text{(II)}$$

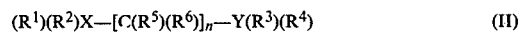

in which X and Y are independently nitrogen, phosphorus, arsenic, antimony or bismuth; n is an integer; ($R^1$), ($R^2$), ($R^3$) and ($R^4$) are independently saturated monovalent organic radicals containing from 1 to 20 carbon atoms. Examples of polydentate ligands which are effective in the production of ethanol are those having the formula (II) in which ($R^1$), ($R^2$), ($R^3$) and ($R^4$) are $C_6H_5-$, X and Y are phosphorus and n has the value 4 to 6.

4 Claims, No Drawings

PROCESS FOR THE PRODUCTION OF ETHANOL AND/OR ACETALDEHYDE BY REACTING METHANOL WITH SYNTHESIS GAS

The present invention relates to a process for the production of ethanol and/or acetaldehyde from methanol and a mixture of carbon monoxide and hydrogen (hereinafter to be referred to as synthesis gas) in the presence of novel catalyst systems.

Both ethanol and acetaldehyde are valuable industrial products. Ethanol is generally manufactured either by fermentation of natural products, eg molasses or by hydration of ethylene in the presence of an acid catalyst such as phosphoric acid. Acetaldehyde is principally produced by the direct oxidation of ethylene or light hydrocarbons, and as a by-product in the production of vinyl acetate. Acetaldehyde is also produced by the vapour phase oxidation or dehydrogenation of ethanol.

The rapidly dwindling reserves of crude oil from which ethylene is derived and the associated need to utilise fully the remaining natural resources such as coal and the vast amounts of gases, eg methane, potentially available from the exploitation of North Sea oilfields has stimulated researchers to investigate other routes to ethanol utilising these materials as feedstocks. Both coal and methane gas can be converted into synthesis gas, which in turn can be reacted to form methanol, which methanol can be further reacted with carbon monoxide and hydrogen in the presence of a water soluble cobalt catalyst and under appropriate conditions to form ethanol or acetaldehyde. The course of these reactions can be represented by the following equations.

$$CH_3OH + CO + 2H_2 \rightarrow C_2H_5OH + H_2O$$

$$CH_3OH + CO + H_2 \rightarrow CH_3CHO + H_2O$$

Earlier prior art processes suffered from the disadvantage that large amounts of by-products such as esters and acids were produced in addition to the desired product. Recently attention has been focussed on methods of suppressing or inhibiting undesirable by-product formation and thereby increasing the total realisable yield and selectivity to ethanol and acetaldehyde. This objective has been to some extent realised by incorporating various additives in the reaction mixture. Thus our Belgian patent No. 867,548 and the specifications accompanying out application Nos 78300608.3 (European) (BP Case No. 4478), and 79300174.4 (European) (BP Case No 4516) describe respectively the addition of an acid and/or an acid derivative, an inert liquid and an oxygen-containing organic solvent to the initial reaction mixture. Also the specification accompanying application No 78300607.5 (European) (Case No 4478/4571) describes the arsenic, antimony or bismuth promoted production of acetaldehyde in the presence of at least one of the additives hereinbefore described. Furthermore GB complete specification No 1546428 describes a process for the production of ethanol in which two elements, (a) a nonpolar solvent and (b) a catalyst comprising a tertiary phosphine, cobalt and an iodide or bromide are said to be essential to the achievement of a higher yield and selectivity. All the foregoing advances utilise, in addition to the soluble cobalt compound, a promoter either as an optional or an essential component of the catalyst system. In addition to bromine and iodine a promoter common to the foregoing is embraced within the following general formula:

wherein X is nitrogen, phosphorus, arsenic, antimony or bismuth and A, B and C are individually monovalent organic radicals, or X is phosphorus, arsenic, antimony or bismuth and any two of A, B and C together form an organic divalent cyclic ring system bonded to the X atom, or X is nitrogen and all of A, B and C together form an organic trivalent cyclic ring system bonded to the X atom.

We have now found that the total realisable yield and selectivity to ethanol and/or acetaldehyde may be increased by the use of a catalyst system comprising cobalt, an iodide or a bromide and a compound containing two or more atoms, which atoms are either identical or combinations of dissimilar atoms of the elements nitrogen, phosphorus, arsenic, antimony or bismuth, with the proviso that no two of the atoms are directly bonded to each other.

The total realisable yield of ethanol within the context of the specification is defined as the yield of free ethanol plus the yield of ethanol realisable by the hydrolysis of ethanol-yielding esters (eg ethyl acetate). In the same way total realisable yield of acetaldehyde is defined as the yield of free acetaldehyde plus the yield of acetaldehyde realisable by the hydrolysis of acetaldehyde-yielding compounds (eg dimethylacetal) and realisable methanol is defined as the free methanol plus the methanol realisable by the hydrolysis of methanol-yielding esters (eg methyl acetate). Thus, % Molar Yield of Realisable Ethanol (Acetaldehyde)

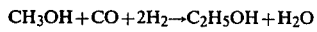

and,

% Molar Selectivity to Realisable Ethanol (Acetaldehyde)

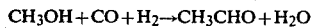

By the yield of realisable acetic acid is meant the yield of free acetic acid plus the yield of acetic acid realisable by the hydrolysis of acetic acid-yielding esters (eg methyl acetate). In calculating the yield it is assumed that all the acetic acid is derived from methanol and synthesis gas and no account is taken of acetic acid derived from cobalt acetate, when this is added as catalyst. Thus, % Molar Yield of Realisable Acetic Acid $$= \frac{\text{Moles of realisable methanol converted into realisable acetic acid} \times 100}{\text{Total moles of realisable methanol fed}}$$

Thus according to the present invention there is provided a process for the production of a product containing ethanol and/or acetaldehyde which process comprises reacting at elevated temperature and pressure methanol with synthesis gas in the presence of a catalyst comprising (a) cobalt, (b) an iodide or a bromide and (c) a polydentate ligand wherein the donor atoms are either identical or combinations of dissimilar atoms of the elements nitrogen, phosphorus, arsenic, antimony or bismuth, with the proviso that no two of the atoms are directly bonded to each other.

In the process of the invention the product will contain:

(i) a substantial proportion of ethanol when the component (c) is a polydentate ligand wherein the donor atoms are exclusively nitrogen or phosphorus;

(ii) a substantial proportion of acetaldehyde when the component (c) is a polydentate ligand wherein the donor atoms are exclusively arsenic, antimony or bismuth, and, (iii) a mixture of ethanol and acetaldehyde when the component (c) is a polydentate ligand wherein at least one of the donor atoms is nitrogen or phosphorus and at least one of the donor atoms is arsenic, antimony or bismuth.

Methanol is a readily available industrial product. It is generally manufactured on an industrial scale from synthesis gas. Whilst it is preferred that the methanol be substantially pure the presence of small amounts of certain impurities can be tolerated. The methanol may however contain up to 50% by weight of water.

Mixtures of the gases hydrogen and carbon monoxide are abundantly available in the form of synthesis gas. Methods for preparing synthesis gas are well known in the art and usually involve the partial oxidation of a carbonaceous substance, e.g. coal. Alternatively synthesis gas may be prpared, for example, by thermal steam reforming of methane. For the purpose of the present invention the molar ratio of carbon monoxide to hydrogen may suitably be in the range 2:1 to 1:3, preferably 1:1 to 1:2. Methods for adjusting the molar ratio of carbon monoxide to hydrogen are well known to those versed in the art. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

With regard to component (a) of the catalyst any source of cobalt which will react with synthesis gas to yield a cobalt carbonyl or carbonyl hydride complex can be used in the process of the present invention. Cobalt is preferably employed in the ionic form, but the use of cobalt metal to react in situ to form ionic cobalt which then further reacts to form the desired cobalt complex is within the scope of the invention. Typical sources of cobalt are, for example, compounds such as cobalt acetate, cobalt formate, cobalt propionate and the like, which under the reaction conditions form carbonyl complexes.

With regard to component (b) of the catalyst the iodide or bromide can be added either in ionic form or as molecular iodine ($I_2$) or bromine ($Br_2$) or as an alkyl or aryl iodide or bromide, preferably methyl iodide. In the ionic form the iodide or bromide may be added as cobalt iodide or cobalt bromide. However, the iodide or bromide may also be added in ionic form utilising cations which are inert with regard to the hydrocarbonylation reaction. Typical of the inert form is potassium iodide or bromide, sodium iodide or bromide and lithium iodide or bromide. Of the iodide or the bromide the iodide is preferred.

With regard to component (c) of the catalyst polydentate ligands are defined in "Advanced Inorganic Chemistry" by Cotton F. A and Wilkinson G, Wiley (USA), 3rd edition 1972, page 140 as ligands having two or more atoms which can simultaneously serve as donors, ligands being defined on page 139 of the same work as any atom, ion or molecule capable of functioning as the donor partner in one or more co-ordinate bonds. The polydentate ligand may suitably be one having the formula:

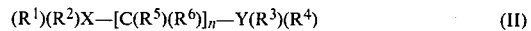
$(R^1)(R^2)X-[C(R^5)(R^6)]_n-Y(R^3)(R^4)$ (II)

wherein X and Y are independently nitrogen, phosphorus, arsenic, antimony or bismuth, n is an integer, $R^1$, $R^2$, $R^3$ and $R^4$ are independently monovalent organic radicals and $R^5$ and $R^6$ are independently either hydrogen atoms or monovalent organic radicals. Preferably the integer n in the compound of formula (II) is in the range 1 to 8, even more preferably 4 to 6. Compounds having the formula (II) may be termed bidentate ligands. Alternatively the polydentate ligand may suitable have the formula:

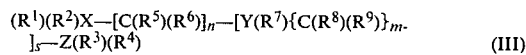
$(R^1)(R^2)X-[C(R^5)(R^6)]_n-[Y(R^7)\{C(R^8)(R^9)\}_m-]_s-Z(R^3)(R^4)$ (III)

wherein X, Y and Z are independently nitrogen, phosphorus, arsenic antimony or bismuth; n, m and s are integers; $R^1$, $R^2$, $R^3$ and $R^4$ are independently monovalent organic radicals and $R^5$, $R^6$, $R^7$, $R^8$ and $R^9$ are independently either hydrogen atoms or monovalent organic radicals.

In addition to the straight-chain polydentate ligands of formula (II) and (III) the polydentate ligand may also have a branched-chain structure. Thus the ligand may have the formula:

(IV)

wherein R is a monovalent organic radical and either M, P and Q are independently the groups $-X(R^1)(R^2)$, $-Y(R^3)(R^4)$ and $-Z(R^{10})(R^{11})$ in which X, Y and Z are independently nitrogen, phosphorus, arsenic, antimony or bismuth and $(R^1)$, $(R^2)$, $(R^3)$, $(R^4)$, $(R^{10})$ and $(R^{11})$ are monovalent organic radicals, or any two of M, P and Q are independently the groups $-X(R^1)(R^2)$ and $-Y(R^3)(R^4)$ and the remaining group M, P or Q is a hydrogen atom or a monovalent organic radical. Another type of branched chain ligand which may be employed in the process of the invention has the formula:

(V)

wherein R is a monovalent organic radical and either S, T and V are independently the groups $-\{C(R^5)(R^6)]_n-X(R^1)(R^2)$, $-\{C(R^8)(R^9)]_m -Y(R^3)(R^4)$, and $-[C(R^{12})(R^{13})]_q-Z(R^{10})(R^{11})$ in which X, Y and Z are independently nitrogen, phosphorus, arsenic, antimony or bismuth; $(R^1)$, $(R^2)$, $(R^3)$, $(R^4)$, $(R^{10})$ and $(R^{11})$ are independently monovalent organic radicals, n, m and q are integers and $(R^5)$, $(R^6)$, $(R^8)$, $(R^9)$, $(R^{12})$ and $(R^{13})$ are independently either hydrogen atoms or monovalent organic radicals or any two of S, T and V are independently the groups $-\{C(R^5)(R^6)]_n-X(R^1)(R^2)$ and ─[C(R$^8$)(R$^9$)]$_m$─Y(R$^3$)(R$^4$) and the remaining group S, T or V is either a hydrogen atom or a monovalent organic radical. Compounds having the formulae (IV) and (V) are examples of bidentate or tridentate ligands.

In the formulae (II), (III), (IV) and (V) above the groups R$^5$, R$^6$, R$^8$, R$^9$, R$^{12}$ and R$^{13}$ are preferably hydrogen atoms. The groups R$^1$, R$^2$, R$^3$, R$^4$, R$^7$, R$^{10}$ and R$^{11}$, and, optionally, the groups M, P, Q, S, T and V, R$^5$, R$^6$, R$^7$, R$^8$, R$^9$, R$^{12}$ and R$^{13}$ are monovalent organic radicals which preferably contain from 1 to 20 carbon atoms and are preferably free from aliphatic carbon-carbon unsaturation. Preferably the groups are hydrocarbyl groups which may be saturated aliphatic, saturated cycloaliphatic, aromatic, substituted saturated aliphatic substituted saturated cycloaliphatic or substituted aromatic groups, of which the unsubstituted groups are preferred. The substituents are preferably free from aliphatic carbon-carbon unsaturation and may contain, besides atoms of carbon and hydrogen, other atoms, such as oxygen, sulphur and halogen, in particular halogen of atomic number from 9 to 35, provided that such atoms are not directly bonded to nitrogen, phosphorus, arsenic, antimony or bismuth.

Illustrative of suitable hydrocarbyl groups are methyl, ethyl, propyl, isopropyl, butyl, isoctyl, decyl, dodecyl, octadecyl, cyclohexyl, cyclopentyl, 3,4-dimethyl cyclopentyl, cyclooctyl, benzyl, β-phenylethyl, phenyl, tolyl, xylyl, p-ethylphenyl, p-tert-butylphenyl, m-octyl phenyl, 2,4-diethylphenyl, p-phenylphenyl, m-benzylphenyl and 2,4,6-trimethylphenyl.

Of the polydentate ligands of formulae (II) to (V) the preferred class of ligand is that having the formula (II). Furthermore for ethanol production it is preferred that both X and Y in the formula (II) are phosphorus.

Illustrative of the polydentate ligands of formula (II) which may be used in the process of the invention are those having the formula (C$_6$H$_5$)$_2$P(CH$_2$)$_g$P(C$_6$H$_5$)$_2$ wherein g is an integer preferably in the range from 1 to 8, even more preferably in the range 4 to 6, of which (C$_6$H$_5$)$_2$P(CH$_2$)P(C$_6$H$_5$)$_2$; (C$_6$H$_5$)$_2$P(CH$_2$)$_4$P(C$_6$H$_5$)$_2$ and (C$_6$H$_5$)$_2$P(CH$_2$)$_6$P(C$_6$H$_5$)$_2$ are exemplary.

The term "hydrocarbyl" has been used throughout the foregoing in its accepted meaning as representing a radical formed from a hydrocarbon by removal of a hydrogen atom.

The exact nature of the catalysts of this invention under the reaction conditions is not known but they are thought to be phosphorus, nitrogen, arsenic, antimony or bismuth-containing ligand/cobalt carbonyl/hydride/halide complexes. The cobalt is thought to be in a reduced state but its exact valency is not known. The catalyst may be prepared by first reacting the individual components together and then adding the catalyst mixture to the reaction vessel, or by adding the individual components to the reaction vessel and allowing the catalyst to form under the reaction conditions. During formation of the arsenic, antimony or bismuth-containing catalyst it may be advantageous to use pressures higher than those employed in the subsequent hydrocarbonylation reaction, particularly when reaction pressures of about 100 bar are employed.

In the presence of nitrogen and phosphorus-containing catalysts methanol may suitably be reacted with carbon monoxide and hydrogen at any temperature in the range 150° to 250°, preferably 180° to 230° C. and at a pressure greater than 80 bars, preferably in the range 100 to 300 bars. In the presence of arsenic, antimony and bismuth-containing catalysts lower reaction temperatures are preferred. Whilst the temperature may be in the range 150° to 250° C., preferably the temperature is in the range 165° to 210°, even more preferably 165° to 198° C.

The process may be carried out batchwise or continuously, continuous operation being preferred. The process may be carried out continuously for example by continuously feeding methanol and synthesis gas to a reactor containing the catalyst, removing from the reactor a liquid product containing ethanol and/or acetaldehyde, by-products, unchanged methanol, catalyst and unreacted synthesis gas, separating the synthesis gas which may be recycled to the reactor, removing light ends including ethers, separating the product containing ethanol and/or acetaldehyde and by-products from the catalyst and thereafter recovering ethanol and/or acetaldehyde from the by-products, there being recycled to the reactor the catalyst and methanol. Other reaction by-products particularly those which can act as precursors for the formation of ethanol and/or acetaldehyde may also be recycled to the reactor with advantage. It may be necessary to feed from time to time further catalyst.

The residence time may suitably be up to 8 hours, but is preferably in the range of from 10 to 180 minutes. Using arsenic, antimony and bismuth-containing catalysts short residence times are preferred because long residence times may lead to further reaction of acetaldehyde by aldol condensation-type reaction giving, for example, n-butyraldehyde. Within the context of the specification the residence time for batchwise operation is that time during which the reactor is at the specified reaction temperature. When the process is operated continuously the residence time is calculated as follows:

$$\text{Residence Time (Hours)} = \frac{\text{Volume of the reactor occupied by the liquid phase at STP (litres)}}{\text{Total flow of liquid into the reactor (litres/hour at STP)}}$$

With regard to the various ratios of reactants to be employed in the process of the invention it has already been stated that the methanol may contain up to 50% by weight of water. The molar ratio of methanol to synthesis gas fed in both continuous and batch operation may be in the range of from 10:1 to 1:20, preferably from 2:1 to 1:5.

In the catalyst the molar ratio of cobalt to iodide or bromide may be in the range from 1:3 to 10:1, preferably from 1:1 to 5:1. The molar ratio of cobalt to component (c) of the catalyst may be in the range of from 1:3 to 1:20, preferably from 1:1 to 1:10 based on the number of mole equivalents of nitrogen, phosphorus, arsenic, antimony or bismuth in the catalyst. The molar ratio of iodide or bromide to component (c) may be in the range of from 2:1 to 1:10, preferably from 1:1 to 1:8 based on the number of mole equivalents of nitrogen, phosphorus, arsenic, antimony or bismuth in the catalyst. The molar ratio of cobalt to methanol may be in the range of from 1:10 to 1:1000, preferably from 1:40 to 1:800.

The methanol may be reacted with synthesis gas in the presence of a deliberately added compound. Thus there may be added an acid and/or an acid derivative having the formula:

(VI)

wherein the substituent R is a hydrocarbyl group or an oxygen containing hydrocarbyl group and the substituent X is the group —OR$^1$ in which R$^1$ is independently a hydrogen atom, a hydrocarbyl group or an oxygen-containing hydrocarbyl group or X is the group —O—CO—R$^2$ wherein R$^2$ is independently a hydrocarbyl group or an oxygen-containing hydrocarbyl group, as described in our published Belgian Patent No. 867548. Suitable compounds having the structural formula (VI) include acetic acid, acetic anhydride, propionic acid, phenylacetic acid, benzoic acid, methyl acetate and butyl acetate. Preferred compounds having the structural formula (VI) are acetic acid and methyl acetate. The acid and/or acid derivative of structural formula (VI) may be added in an amount such that the molar ratio of acid and/or acid derivative to free methanol can be as high as 1.5:1, more usually in the range of from 0.1:1 to 0.7:1.

Alternatively, or in addition, the additive may be an inert liquid which is an aryl halide, a thiophene, a long chain acid or a silicone oil. An example of a suitable aryl halide is chlorobenzene. A suitable example of a long chain acid is decanoic acid. Typical of the silicone oils which may be used are polydimethylsiloxane fluids and methyl phenyl silicone fluids. Specific silicone fluids which have been found useful in the process are the DC 200 series of fluids supplied by Dow Corning. In certain circumstances the addition of water may be beneficial to the reaction ie the ratio of methanol to water in the feed can be adjusted so that two phases are present either at the start or at the end of the reaction or both. The molar ratio of methanol to inert liquid can be varied within wide limits, e.g. from 30:1 to 1:10, preferably from 25:1 to 1:2.

Alternatively, or in addition, there may be added an oxygen-containing organic compound comprising compounds containing at least one of the groups:

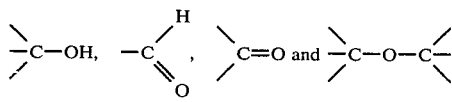

which compound preferably exists mainly in the form of a liquid under the reaction conditions employed. Whilst the oxygen-containing organic compound containing a

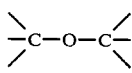

group may be an aliphatic, alicyclic or aromatic ether it is preferred that those compounds containing

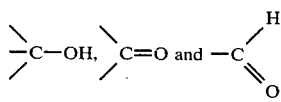

groups are, respectively, aliphatic alcohols, aliphatic ketones and aliphatic aldehydes. Oxygen-containing organic compounds which may be added include, for example, 1,4-dioxane, tetrahydrofuran, di-n-propylether, diphenylether, acetone, acetaldehyde, n-propanol and n-butanol. The oxygen-containing organic compound may be added in an amount such that the molar ratio of methanol to the oxygen-containing organic compound is in the range from 20:1 to 1:3, preferably from 10:1 to 1:1.

Alternatively, or in addition, the additive may be a non-polar solvent. Suitable non-polar solvents include alkanes, benzene and alkyl-substituted benzenes as disclosed in US patent application Serial No. 585276. The molar ratio of methanol to non-polar solvent may suitably be in the range of from 30:1 to 1:10, preferably from 25:1 to 1:2.

Alternatively, or in addition, the solvent may be a co-ordinating solvent, such as sulpholane in the proportions as described hereinbefore for inert and polar-solvents addition.

Whilst it is appreciated that both acids and acid derivatives having the formula (VI) and oxygen-containing organic compounds may be formed as by-products during the course of the reaction one aspect of the present invention resides in the addition of one or other or both to the reaction. By so-doing the amount of undesirable side-reaction is reduced, with the attendant consequence that the yield and selectivity to ethanol and/or acetaldehyde is increased.

In addition, in the presence of nitrogen and phosphorus-containing catalysts, it may be advantageous to add certain metal co-catalysts. Thus, for example the addition of ruthenium compounds, such as Ru$_3$(CO)$_{12}$, RuI$_3$ and RuCl$_3$.xH$_2$O, may increase the yield of realisable ethanol and improve the selectivity to ethanol by reducing the amount of undesirable side-reaction. The molar ratio of cobalt compound to ruthenium compound may suitably be in the range 100:1 to 1:1.

The invention will now be illustrated by reference to the following Examples.

COMPARISON TEST A

A stainless steel, magnetically-stirred autoclave equipped for pressurised reactions was charged under nitrogen with methanol (7.99 moles) containing cobalt acetate tetrahydrate (0.10 moles) and iodine (0.05 moles). The system was purged with nitrogen, then pressurised to 120 bars (roughly equivalent to a pressure of 200 bars at 190° C.) with a mixture of carbon monoxide and hydrogen (1 mole carbon monoxide to 2 moles hydrogen). The reactor temperature was then raised to 190° C. and maintained at this value for 2 hours. When heating was started the pressure in the reactor rose above 120 bars. As soon as the reaction commenced the rate of increase in the pressure began to decrease. It was therefore necessary to make periodic injections of the carbon monoxide/hydrogen mixture to compensate for the gas consumed by the reaction and maintain the rate of pressure increase in accord with achieving a pressure of 200 bars at 190° C. When this objective was achieved the pressure was maintained at a value of 200 bars throughout the reaction by continuously feeding fresh carbon monoxide and hydrogen (1:2 molar mixture) to the autoclave. After 2 hours at 190° C. the autoclave was allowed to cool and the reaction product was analysed. The amounts of reactants are given in Table 1A and the results in Table 1B.

This is not an example according to the present invention because of the absence of the essential component (c) of the catalyst. It is included only for the purpose of comparison.

COMPARISON TEST B

The procedure of Comparison Test A was repeated except that triphenyl phosphine was added to the autoclave with the initial charge. The amounts of reactants are given in Table 1A and the results in Table 1B.

This is not an example according to the present invention because triphenyl phosphine contains only one atom of phosphorus. It is included for the purpose of comparison only.

EXAMPLE 1

The procedure of Comparison Test A was repeated except that $(C_6H_5)_2P(CH_2)_6P(C_6H_5)_2$ was added to the autoclave in the initial methanol charge. The amounts of reactants are given in Table 1A and the results in Table 1B.

COMPARISON TEST C

The procedure of Comparison Test A was repeated except that acetone and triphenyl phosphine were included in the initial reaction mixture fed to the autoclave. The amounts of reactants are given in Table 2A and the results in Table 2B.

This is not an example according to the present invention because triphenyl phosphine contains only one atom of phosphorus. It is included only for the purpose of comparison.

EXAMPLE 2

The procedure of Comparison Test A was repeated except that acetone and $(C_6H_5)_2P(CH_2)P(C_6H_5)_2$ were included in the initial reaction mixture fed to the autoclave. The amounts of reactants are given in Table 2A and the results in Table 2B.

EXAMPLE 3

The procedure of Comparison Test A was repeated except that acetone and $(C_6H_5)_2P(CH_2)_4P(C_6H_5)_2$ were included in the initial reaction mixture fed to the autoclave. The amounts of reactants are given in Table 2A and the results in Table 2B.

EXAMPLE 4

The procedure of Comparison Test A was repeated except that acetone and $(C_6H_5)_2P(CH_2)_6P(C_6H_5)_2$ were included in the initial reaction mixture fed to the autoclave. The amounts of reactants are given in Table 2A and the results in Table 2B.

COMPARISON TEST D

A stainless steel, magnetically-stirred autoclave equipped for pressurised reactions was charged under nitrogen with methanol (1.78 moles) containing cobalt acetate tetrahydrate (0.0225 mole), iodine (0.0113 mole) and triphenylphosphine (0.0394 mole). To this mixture was further added 0.071 mole chlorobenzene. The system was purged with nitrogen, then pressurised to 200 bars with a mixture of carbon monoxide and hydrogen (1:1 molar). The reactor temperature was then raised to 205° C. and maintained at this temperature for 2 hours. When heating was started the pressure in the reactor rose above 200 bars and then began to decrease as the reaction commenced. During the course of the reaction, whenever the pressure in the autoclave fell to 140 bars a fresh charge of carbon monoxide and hydrogen (1:1 molar mixture) was added thereby increasing the reactor pressure to 200 bars. After two hours at 205° C. the autoclave was allowed to cool and the reaction product was analysed. The amounts of reactants are given in Table 3A and the results in Table 3B. This is not an example according to the invention because triphenylphosphine contains only one atom of phosphorus. It is included only for the purpose of comparison.

EXAMPLE 5

The procedure of Comparison Test D was repeated except that triphenyl phosphine was replaced by $(C_6H_5)_2P(CH_2)_6P(C_6H_5)_2$. The amounts of reactants are given in Table 3A and the results in Table 3B.

It can be seen from the results set out in Table 1B that the addition of triphenylphosphine to the catalyst system as a promoter increases the total realisable yield and selectivity to ethanol. When the triphenylphosphine is replaced by a promoter containing two atoms of phosphorus, i.e. $(C_6H_5)_2P(CH_2)_6P(C_6H_5)_2$ there is a further significant increase in total realisable yield and selectivity to ethanol.

From the results set out in Table 2B it can be seen that the addition of an oxygen-containing organic solvent, in this case acetone, to the triphenylphosphine promoted catalyst increases the total realisable yield and selectivity to ethanol. Furthermore replacement of triphenylphosphine in the acetone-containing reaction system by a compound of the type $(C_6H_5)_2P(CH_2)_nP(C_6H_5)_2$, wherein n is an integer, further increases the total realisable yield and selectivity to ethanol. Moreover the increase becomes larger as the value of n increases.

Finally from the results shown in Table 3B it can be seen that replacement of the triphenylphosphine promoter by $(C_6H_5)_2P(CH_2)_6P(C_6H_5)_2$ in the system containing also an inert solvent, in this case chlorobenzene, increases the total realisable yield and selectivity to ethanol.

TABLE 1A

| | | Reactor Feed | | | | |
|---|---|---|---|---|---|---|
| | | Inert Liquid | | Catalyst | | |
| Example (A) | CH$_3$OH (moles) (B) | Nature (C) | No of moles (D) | (a) Cobalt (moles × 10$^{-3}$) (E) | (b)I$_2$ (moles × 10$^{-3}$) (F) | (c) Ligand (moles × 10$^{-3}$) (G) |
| Comp Test A | 7.99 | None | None | Co(OAc)$_2$4H$_2$O (100.0) | 50.0 | None |
| Comp Test B | 1.80 | None | None | Co(OAc)$_2$4H$_2$O (22.5) | 11.3 | P(C$_6$H$_5$)$_3$ (39.3) |
| 1 | 1.99 | None | None | Co(OAc)$_2$4H$_2$O (25.0) | 12.5 | (C$_6$H$_5$)$_2$P(CH$_2$)$_6$P(C$_6$H$_5$)$_2$ (21.9) |

TABLE 2A

| (A) | (B) | (C) | (D) | (E) | (F) | (G) |
|---|---|---|---|---|---|---|
| Comp Test C | 1.80 | Acetone | 0.145 | Co(OAc)$_2$4H$_2$O (22.5) | 11.3 | P(C$_6$H$_5$)$_3$ (39.3) |
| 2 | 1.80 | Acetone | 0.145 | Co(OAc)$_2$4H$_2$O (22.5) | 11.3 | (C$_6$H$_5$)$_2$P(CH$_2$)P(C$_6$H$_5$)$_2$ (19.7) |
| 3 | 1.80 | Acetone | 0.145 | Co(OAc)$_2$4H$_2$O (22.5) | 11.3 | (C$_6$H$_5$)$_2$)$_4$P(C$_6$H$_5$)$_2$ (19.7) |
| 4 | 1.80 | Acetone | 0.145 | Co(OAc)$_2$4H$_2$O (22.5) | 11.3 | (C$_6$H$_5$)$_2$P(CH$_2$)$_6$P(C$_6$H$_5$)$_2$ (19.7) |

TABLE 3A

| (A) | (B) | (C) | (D) | (E) | (F) | (G) |
|---|---|---|---|---|---|---|
| Comp Test D | 1.78 | Chlorobenzene | 0.071 | Co(OAc)$_2$4H$_2$O (22.5) | 11.3 | P(C$_6$H$_5$)$_3$ (39.4) |
| 5 | 1.81 | Chlorobenzene | 0.072 | Co(OAc)$_2$4H$_2$O (22.5) | 11.3 | (C$_6$H$_5$)$_2$P(CH$_2$)$_6$P(C$_6$H$_5$)$_2$ (19.7) |

TABLE 1B

| | % Molar yields on methanol fed | | | | | % Molar yield CH$_4$ + CO$_2$ ** (N) | % Molar selectivity to realisable C$_2$H$_5$OH (O) | % CH$_3$OH conversion (P) |
|---|---|---|---|---|---|---|---|---|
| Example (H) | Realisable C$_2$H$_5$OH (I) | Realisable CH$_3$COOH (J) | Dimethyl acetal * (K) | CH$_3$CHO (L) | n-C$_3$H$_7$OH + n-C$_4$H$_9$OH (M) | | | |
| Comp Test A | 4.2 | 4.1 | 6.4 | 1.2 | <1 | 19.2 | 11.4 | 36.7 |
| Comp Test B | 18.9 | 3.3 | 8.9 | 2.0 | 1.8 | 7.0 | 41.9 | 45.1 |
| 1 | 32.9 | 2.6 | 5.2 | <1 | 1.2 | 9.3 | 65.0 | 50.6 |

*Dimethyl acetal is 1,1-dimethoxy ethane
**The % molar yield of methane + carbon dioxide is calculated on the carbon monoxide fed to the reaction.

TABLE 2B

| (H) | (I) | (J) | (K) | (L) | (M) | (N) | (O) | (P) |
|---|---|---|---|---|---|---|---|---|
| Comp Test C | 24.7 | 3.8 | 9.0 | 2.2 | 1.5 | 8.9 | 46.2 | 53.5 |
| 2 | 28.0 | 4.0 | 8.6 | 2.0 | 1.5 | 12.2 | 53.8 | 52.0 |
| 3 | 31.8 | 4.1 | 6.8 | 1.1 | 1.3 | 9.3 | 58.9 | 54.0 |
| 4 | 34.3 | 4.3 | 6.5 | <1 | 1.4 | 8.8 | 66.7 | 51.4 |

TABLE 3B

| (H) | (I) | (J) | (K) | (L) | (M) | (N) | (O) | (P) |
|---|---|---|---|---|---|---|---|---|
| Comp Test D | 29.0 | 10.1 | 3.5 | 1.3 | 2.5 | 9.3 | 44.8 | 64.8 |
| 5 | 36.3 | 7.3 | 6.1 | 1.2 | 2.7 | 20.3 | 56.2 | 64.6 |

We claim:

1. A process for the production of a product containing ethanol which process comprises reacting at a temperature in the range of about 180° to 230° C. and a pressure in the range of about 100 to 300 bars methanol with synthesis gas in the presence of a catalyst comprising:
   (a) cobalt
   (b) an iodide or a bromide, and
   (c) a polydentate ligand selected from ligands having the formula:

$$(C_6H_5)_2P(CH_2)_gP(C_6H_5)_2$$

wherein g is an integer having a value in the range 1 to 8.

2. A process according to claim 1 wherein said catalyst additionally contains a ruthenium compound in an amount such that the molar ratio of said cobalt to said ruthenium compound is in the range from about 100:1 to 1:1.

3. A process according to claim 1 wherein the molar ratio of said methanol to said synthesis gas is in the range from 10:1 to 1:20, the molar ratio of said cobalt to said iodide or bromide is in the range from 1:3 to 10:1, the molar ratio of said cobalt to said polydentate ligand based on the number of mole equivalents of said donor atoms in said ligand is in the range from 1:3 to 1:20, the molar ratio of said iodide or bromide to said polydentate ligand based on the number of mole equivalents of said donor atoms in said ligand is in the range from 2:1 to 1:10, the molar ratio of said cobalt to said methanol is in the range from 1:10 to 1:1000 and the molar ratio of carbon monoxide to hydrogen in said synthesis gas is in the range from 2:1 to 1:3.

4. A process according to claim 1 wherein said polydentate ligand is selected from (C$_6$H$_5$)$_2$P(CH$_2$)P(C$_6$H$_5$)$_2$, (C$_6$H$_5$)$_2$P(CH$_2$)$_4$P(C$_6$H$_5$)$_2$ and (C$_6$H$_5$)$_2$P(CH$_2$)$_6$P(C$_6$H$_5$)$_2$.

* * * * *

UNITED STATES PATENT AND TRADEMARK OFFICE
CERTIFICATE OF CORRECTION

PATENT NO. : 4,262,154
DATED : April 14, 1981
INVENTOR(S) : Brian R. Gane and David G. Stewart It is certified that error appears in the above-identified patent and that said Letters Patent are hereby corrected as shown below:

Col. 1, line 49 - "out" should read --our--.

Col. 2, lines 55 to 60 - after equation, insert second equation as follows: -- % Methanol conversion $$= \frac{\text{Total moles of methanol converted}}{\text{Total moles of methanol fed}} \times 100 \text{ --}$$

Col. 3, line 29 - correct spelling of "prepared".

Col. 4, lines 59, 60 and 68, and Col. 5, line 1 - before each occurrence of "C(R", delete "$\neq$", and insert --$\frac{}{}$-- in lieu thereof.

Col. 10, line 46 - after "P(C$_6$H", delete --$_d$--.

Signed and Sealed this

Twenty-eighth Day of July 1981

[SEAL]

Attest:

GERALD J. MOSSINGHOFF

Attesting Officer    Commissioner of Patents and Trademarks